Figure 3:
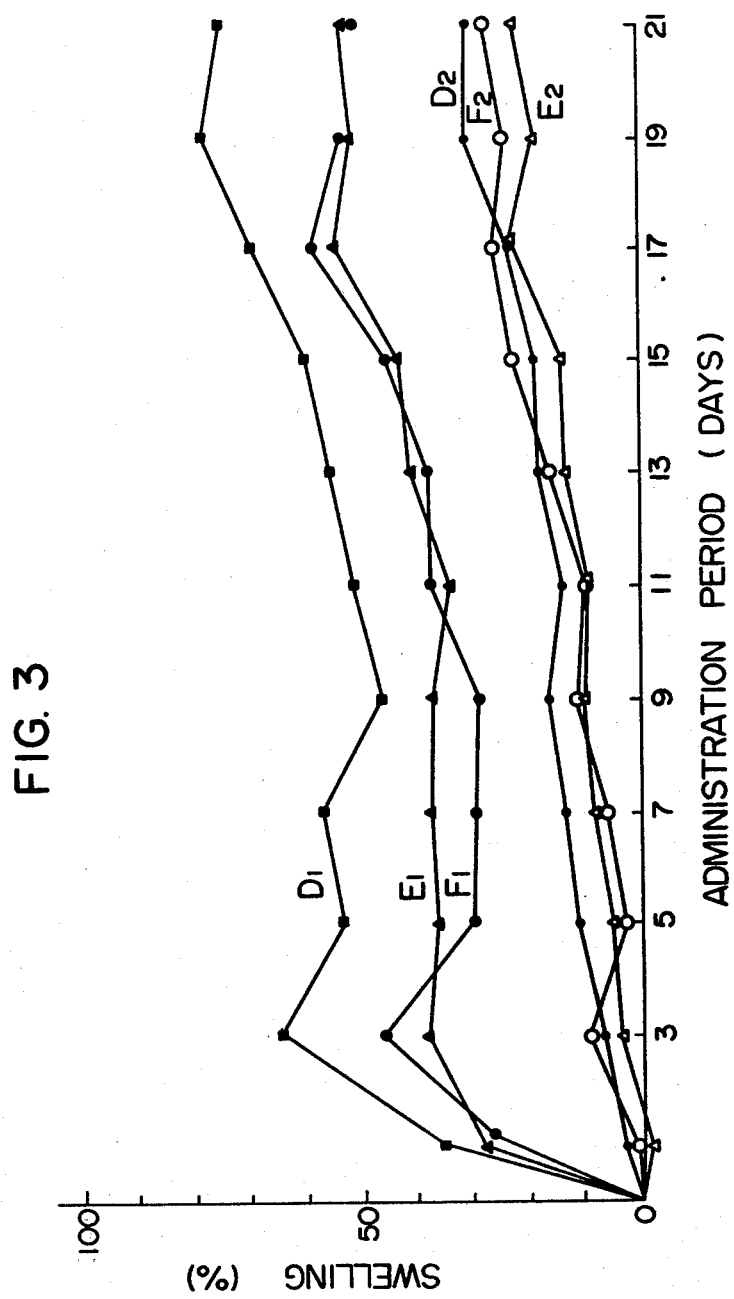

United States Patent [19]

Aonuma

[11] 4,310,521
[45] Jan. 12, 1982

[54] ASPIRIN-ISOPROPYLANTIPYRINE

[75] Inventor: Shinichiro Aonuma, Hirakata, Japan

[73] Assignee: Toho Pharmaceutical Co., Ltd., Tokyo, Japan

[21] Appl. No.: 204,788

[22] Filed: Nov. 7, 1980

[30] Foreign Application Priority Data

Nov. 9, 1979 [JP] Japan .................................. 54-144325

[51] Int. Cl.³ .......................................... A61K 31/625
[52] U.S. Cl. .................................... 424/232; 548/368
[58] Field of Search ................ 548/367, 368; 424/232

[56] References Cited

U.S. PATENT DOCUMENTS 2,891,070  6/1959  Ledrut ................................. 548/367

OTHER PUBLICATIONS

Shabrova et al., Chem. Abst. 1964, vol. 61, p. 3089h.
Shabrova et al., Chem. Abst. 1971, vol. 74, No. 125,549v.

Primary Examiner—Henry R. Jiles
Assistant Examiner—Natalia Harkaway
Attorney, Agent, or Firm—Wenderoth, Lind & Ponack

[57] ABSTRACT

Aspirin-isopropylantipyrine (N-3'a-propylphenazonyl-2-acetoxybenzamide) of the following formula

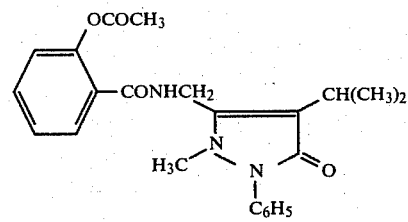

and its pharmaceutical use. This compound can be prepared by reacting 1-phenyl-2-methyl-3-aminomethyl-4-isopropylpyrazolone of the formula

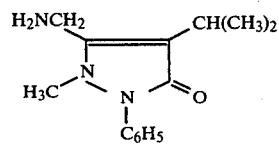

with a member selected from the group consisting of acetylsalicylic acid and a reactive acid derivative thereof, and is useful as an analgetic, antipyretic and anti-inflammatory agent.

4 Claims, 3 Drawing Figures

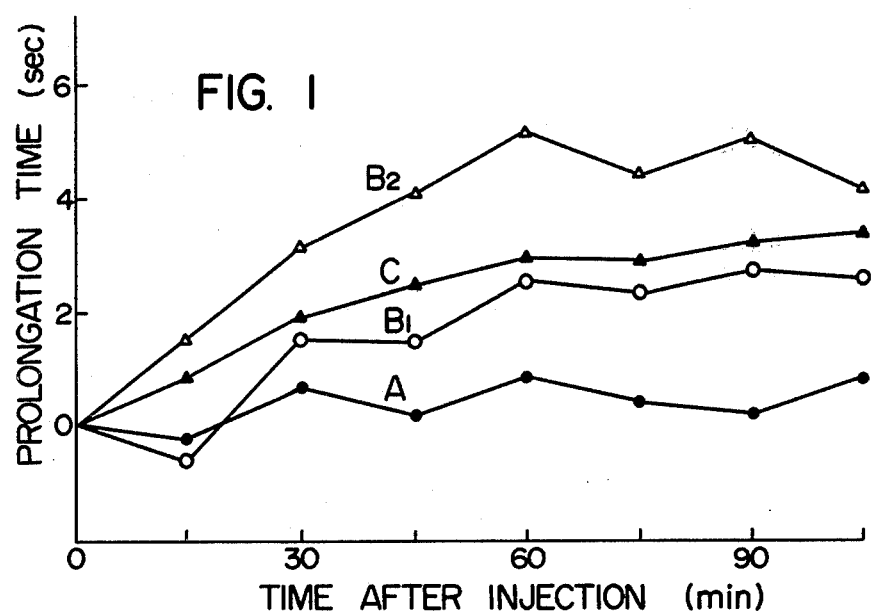
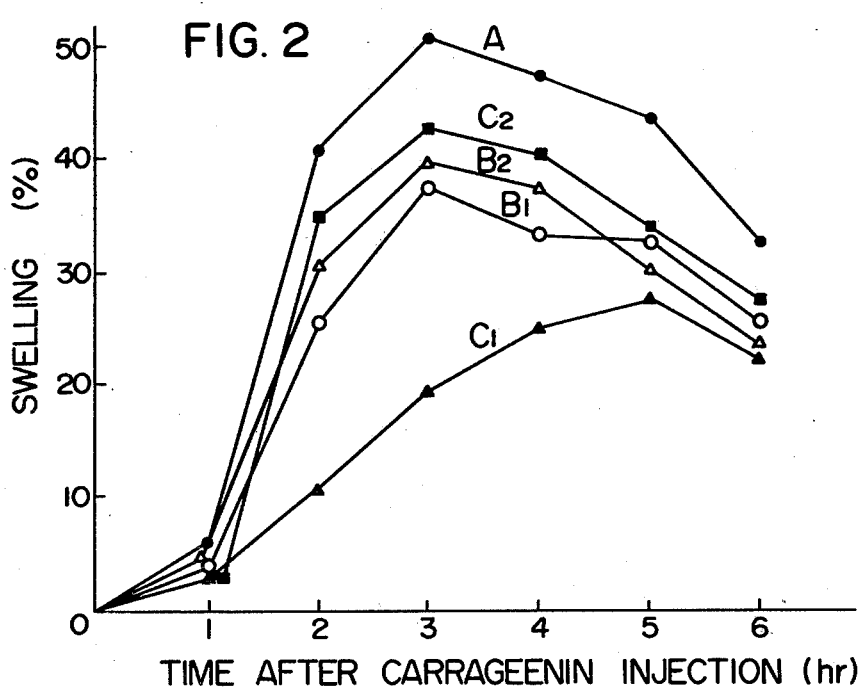

ASPIRIN-ISOPROPYLANTIPYRINE

This invention relates to aspirin-isopropylantipyrine (N-3'a-propylphenazonyl-2-acetoxybenzamide), a compound that has yet to be found in known literature, a process for producing same, and its utilization as an analgetic, antipyretic and anti-inflammatory agent.

More specifically, this invention relates to aspirin-isopropylantipyrine of the following formula

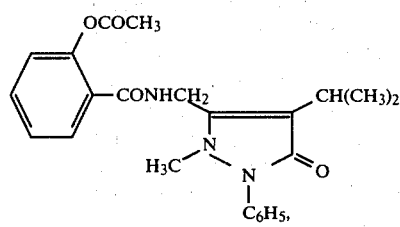

a process for producing the compound of formula (I), and its utilization for medicinal purposes.

Aspirin (acetylsalicylic acid) is being widely used as a relatively safe antipyretic, analgetic and anti-inflammatory agent. It however has the drawback that it has a gastric ulcerogenic activity, with the consequence that it causes nausea and loss of appetite and even induces such gastric disorders as peptic ulcer, hemorrhage of stomach, etc. at times. Especially, in the case where aspirin is administered in large doses say for treatment of rheumatic diseases, care must be exercised to guard against gastric disorders ascribable to the ingestion of aspirin. Furthermore, aspirin is hygroscopic, and hence aspirin not only is decomposed by moisture but when it is mixed with other drugs, for example, other antipyretic and analgetic preparations, it becomes moist and discolored at times.

We previously found that the toxicity of isopropylantipyrine, a pyrazolone-type antipyretic and analgetic preparation, could be reduced and its stability could be enhanced without diminishing its antipyretic and analgetic activities by introducing a substituent to the 3-methyl group of isopropylantipyrine.

Our further researches led to the discovery that by introducing the acetylsalicylamide group to the 3-position methyl group there is produced a novel compound not found in prior literature, and that this compound can be synthesized in good yield by a simple procedure.

It was also found that this novel compound that can be expressed by the foregoing formula (I), while possessing superior analgetic, antipyretic and anti-inflammatory activity, demonstrates a marked reduction of such activities as cause gastric disorders that are possessed by aspirin and the side effects of the pyrazolone-type antipyretic and analgetic preparations. Moreover, it is not hygroscopic. It is hence a unique compound possessing good stability.

An object of this invention is therefore to provide a compound of the foregoing formula (I). Another object is to provide a process for producing the compound of formula (I), as well as methods of its utilization.

The foregoing objects and other objects and advantages of the present invention will become apparent from the following description.

The aspirin-isopropylantipyrine of formula (I) of this invention can be prepared by reacting 1-phenyl-2-methyl-3-aminomethyl-4-isopropylpyrazolone of the formula

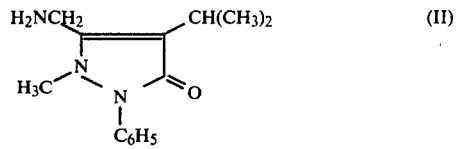

with either acetylsalicylic acid or a reactive acid derivative thereof.

The formula (II) compound can be obtained by reacting the compound of the formula

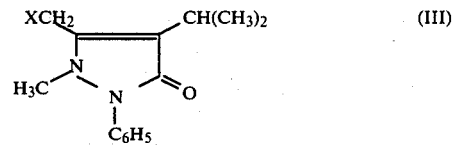

wherein X is halogen, with hexamethylenetetramine followed by hydrolysis of the product and thereafter reacting the product with ammonia. Examples of the halogen atoms of X in the foregoing formula (III) are, for example, Cl, Br and I.

The reaction between the formula (III) compound and hexamethylenetetramine can be carried out preferably in an inert solvent, for example in chloroform, at elevated temperatures, preferably at the reflux temperature. The reaction mole ratio can be suitably chosen. For example, the hexamethylenetetramine can be used in an amount of about 1.0 moles to about 1.2 moles per mole of the compound of formula (III).

After having reacted the hexamethylenetetramine with the formula (III) compound in the manner described hereinabove, the reaction product is hydrolyzed. The hydrolysis is preferably carried out by the acid hydrolysis technique. Acids that can be used include such mineral acids as hydrochloric acid. The hydrolysis can be carried out in an aqueous medium at, for example, a temperature of about 10° C. to about 25° C.

The reaction between the product thus obtained and ammonia can be carried out in the presence of a suitable inert solvent, for example, chloroform by blowing ammonia gas into the reaction mixture. The reaction can be carried out at a temperature, for example, of about 0° C. to about 20° C. The amount and rate at which the ammonia gas is blown in can be suitably chosen. For example, an amount sufficient to form $H_2NH_2C$ by the de-HX reaction between X and ammonia at the 3-position $XH_2C$ of the formula (III) compound will do. The resulting formula (II) compound can be directly reacted with acetylsalicylic acid or a reactive acid derivative thereof, but it is preferably used after its purification. The purification can be performed by optional means, for example, by chromatography.

In accordance with another mode, the formula (II) compound can also be obtained by reacting the formula (III) compound directly with ammonia. This amination reaction can be carried out by using, for example, an alcohol saturated with ammonia gas. Alcohols that can be used in this mode include such alcohols as ethanol and methanol. The reaction can be carried out, for example, by saturating ethanol with ammonia gas, adding IABr(III) and stirring the mixture at room temperature for 2 hours.

The formula (I) aspirin-isopropylantipyrine of this invention can be obtained by reacting the formula (II) compound thus obtained with acetylsalicylic acid or a reactive acid derivative thereof. As the reactive acid derivatives of acetylsalicylic acid, there can be mentioned, for example, the acid halides such as chloride and bromide; acid anhydride; and the esters such as the lower alcohol esters (e.g. p-nitrophenylester, N-phthalimide ester).

The reaction can be carried out in a suitable inert solvent, for example in chloroform. The reaction is preferably performed in the presence of a carbodiimide such as dicyclohexylcarbodiimide in accordance with the method which per se is known in the synthesis of peptides. The reaction mole ratio can be suitably chosen. For example, the acetylsalicylic acid or reactive acid derivative thereof can be used in an amount of about 1.0 moles to about 1.2 moles per mole of the formula (II) compound. The resulting formula (I) aspirin-isopropylantipyrine can be purified, for example, by chromatography.

The novel compound of formula (I) obtained as above described possesses superior analgetic, antipyretic and anti-inflammatory activity, and moreover the gastric ulcerogenic activity and hygroscopicity that are possessed by aspirin are greatly reduced. In addition, there is a reduction in the side effects that result when the pyrazolone derivatives possessing antipyretic and analgetic activity are used. It is thus seen that the formula (I) aspirin-isopropylantipyrine is extremely useful as an analgetic, antipyretic and anti-inflammatory agent.

It is thus possible to provide in accordance with this invention a pharmaceutical composition composed of pharmaceutically effective amounts of aspirin-isopropylantipyrine of formula (I) and a pharmaceutically acceptable carrier or diluent.

As the carrier or diluent, the various liquid or solid carriers or diluents can be used. As examples, there can be named such solid carriers or diluents as lactose, starch, CMC-Na, magnesium stearate and glucose; and such liquid carriers or diluents as propylene glycol, mucilage of acacia, CMC-Na solution, and ethanol.

Various other adjuvants that are usually used in compounding medicines can also be added.

The pharmaceutical composition of this invention can be prepared in such various forms for oral administration, as powders, granules, pills, tablets, sugar-coated pills, capsules, solutions and suspensions, and such forms for extrabuccal administration as injections and suppositories.

The amount used of the active ingredient of formula (I) in the pharmaceutical composition of this invention can be suitably chosen. For example, the amount used can be about 10% to about 100%, preferably about 99%, by weight based on the weight of the composition. The active ingredient of formula (I) can also be administered not in the form of a composition, but alone.

The pharmaceutical composition of this invention may contain various other drugs such as antipyreticanalgesic drugs (aminopyrine, antipyrine) and ammonium bicarbonate. The compound of formula (I) of this invention has the advantage that no trouble results in using it conjointly with other drugs, since the formula (I) compound is in itself free of hygroscopicity and is stable.

There is also provided in accordance with this invention a method of treating patients needing an analgetic, antipyretic or anti-inflammatory treatment, the method being characterized by the administration of aspirin-isopropylantipyrine of formula (I).

According to this method, the pharmaceutical composition in a form such as hereinbefore described or the formula (I) compound itself can be administered in a dose of about 0.02 to about 0.08 g/kg-body/day. The composition of the invention can be administered through various routes. Thus, it may be in an orally administrable form, an injectable form, or a parenterally administrable form (e.g., suppository).

Tests of the analgetic, antipyretic and anti-inflammatory adtivities as well as acute toxicity of the aspirin-isopropylantipyrine (AIA), the formula (I) compound of this invention, that were conducted using aspirin as comparison will now be described, along with the results obtained.

(1) Analgetic Activity

The number of writhings that occurred when mice were administered an acetic acid solution intraperitoneally were counted, and the rate of inhibition based on the control group was calculated. The test compounds were administered to the mice 30 minutes before the acetic acid solution was administered. The results obtained are shown in Table 1, below. It is seen that the compound of this invention demonstrates an analgetic activity comparable to that of aspirin.

Further, the prolongation time of pain threshold of mouse tail was determined in accordance with the D'Amour-Smith Method (J. Pharmacol. Exp. Ther., 72, 74 (1941)). After the subcutaneous administration of the test compounds to mice, the tails of mice were exposed to heat and the prolongation time of pain threshold was determined. The results obtained are shown in FIG. 1. Curve A in the figure shows the results obtained in the case of the control group; $B_1$, the group administered 100 mg/kg of AIA; $B_2$, the group administered 200 mg/kg of AIA; and C, the group administered 200 mg/kg of aspirin. The group administered 200 mg/kg of AIA was seen to exhibit a stronger analgetic activity than the group administered 200 mg/kg of aspirin.

TABLE 1

| Compound | dose (mg/kg) | No. of Writhings | Inhibition (%) |
|---|---|---|---|
| Control | 0 | 32.2 ± 3.7 | — |
| AIA | 50 | 22.1 ± 3.3 | 31.4 |
|  | 100 | 18.3 ± 1.7 | 43.2 |
| Aspirin | 50 | 17.2 ± 4.0 | 46.6 |
|  | 100 | 15.3 ± 2.4 | 52.5 |

(2) Gastric Ulcerogenic Activity

Immediately after ligation of the pylorus of fasted rats, the test compounds were administered orally. The stomachs were removed 7 hours later, and the lengths of the lesions in the glandular portion were measured. The results obtained are shown in Table 2A, below.

On the other hand, after administering an adjuvant, the rats were orally administered 200 m/kg of the test compounds per day for 21 days. On the 21st day the stomachs were removed, and the lengths of the lesions in the glandular portion were measured. The results obtained are shown in Table 2B, below.

TABLE 2A

| | Gastric Ulcerogenic Activity (Pylorus-ligated rats) | |
|---|---|---|
| Compound | Dose (mg/kg) | Length of Stomach Lesion (cm) |
| AIA | 100 | 0.11 ± 0.09 |
| Aspirin | 100 | 4.13 ± 1.24 |

TABLE 2B

| | Gastric Ulcerogenic Activity (Adjuvant-administered rats) | |
|---|---|---|
| Compound | Dose (mg/kg) | Length of Stomach Lesion (cm) |
| Control | 0 | 0.05 ± 0.048 |
| AIA | 200 | 0.04 ± 0.031 |
| Aspirin | 200 | 3.29 ± 1.37* |

*$P < 0.05$

As is apparent from the results shown in the foregoing Tables 2A and 2B, little or no injury is caused to the stomach by the compound of this invention. It can thus be seen that the gastric ulcerogenic activity possessed by aspirin has clearly disappeared.

(3) Anti-inflammatory Activity

Rats were subcutaneously administered the test compounds, and 30 minutes later a carrageenin solution was administered subcutaneously to the foot pad of the rats. The volume of the hind paw was measured at prescribed intervals after the administration of the carrageenin, and the rate of increase in the volume of the paw was calculated and designated as the rate of swelling (%). The results obtained are shown in FIG. 2. In the figure, curve A shows the results obtained in the case of the control group; $B_1$, the group administered 100 mg/kg of AIA; $B_2$, the group administered 50 m/kg of AIA; $C_1$, the group administered 100 mg/kg (0.56 millimole) of aspirin; and $C_2$, the group administered 50 mg/kg of aspirin.

On the other hand, an adjuvant was administered subcutaneously to only the foot pad of the left hind paw, and 200 mg/kg per day of the test compounds were administered daily for 21 days. The rate of increase in the volume of the both hind paws were measured daily and designated as the rate of swelling (%). The results obtained are shown in FIG. 3. Curve $D_1$ in the figure shows the results obtained in the case of the left hind paws of the control group (adjuvant administered); $D_2$, the right hind paws of the control group (adjuvant not administered); $E_1$, the left hind paws of the AIA-administered group; $E_2$, the right hind paws of the AIA-administered group; $F_2$, the right hind paws of the group administered aspirin.

It is seen from these results that the compound of this invention has the activity of inhibiting carrageenin edema formation and that it has an inhibitory effect on adjuvant arthritis comparable to that of aspirin.

(4) Antipyretic Activity

Rats received a sterilized *E. coli* suspension (1 platinum loop/2 ml saline, 0.5 ml/100 g, i.v.) as a pyrogen, and 2 hours later the test compounds were injected subcutaneously. The temperature was taken at hourly intervals before and after injection of the test compounds.

The compound of this invention demonstrated antipyretic activity in the above test by the subcutaneous administration of 100 mg/kg of the compound.

(5) Additional Activity

The compound of this invention was seen to inhibit the contraction induced in the excised intestinal tract of rats by histamine, acetylcholine and barium chloride, with a concentration of 100 μg/ml.

(6) Acute Toxicity

The acute toxicity of AIA was tested using male mice (ddy, body weight 18–25 g), and the dose at which 50% of the animal population were killed (LD 50) was determined. The results obtained are shown in Table 3. It is seen that the toxicity of AIA is extremely low as compared with that of aspirin.

TABLE 3

| | Acute Toxicity LD 50 (g/kg) | | |
|---|---|---|---|
| Compound | Oral administration | Subcutaneous administration | Intraperitoneal administration |
| AIA | >5.0 | >5.0 | 3.67 ± 0.07 |
| Aspirin | 11.6 ± 0.07 | 1.02 ± 0.11 | 0.76 ± 0.09 |

EXAMPLE 1

Production of Compound (a) Chloroform (180 ml) was added to 30.9 g (0.1 mole) of 2-methyl-3-bromomethyl-1-phenyl-4-isopropylpyrazolone (III) and 14.7 g (0.105 mole) of hexamethylenetetramine, and the mixture was refluxed for 2.5 hours. The chloroform was then distilled off under reduced pressure, after which 600 ml of an ethanol/hydrochloric acid (1:1) mixture was added, and the reaction mixture was stirred at room temperature of 36 hours. After completion of the hydrolysis, the solvent was distilled off under reduced pressure. This was followed by the addition of 500 ml of chloroform and blowing of ammonia gas into the mixture. The resulting precipitate of ammonium chloride was filtered off. After the filtrate was concentrated under reduced pressure, chloroform was added and the operation of concentrating under reduced pressure was repeated five times to eliminate the remaining ammonia.

After dissolving the resulting concentrate in 100 ml of chloroform, the solution was added to a column packed with B 1.4 liters of silica gel (WAKOGEL C-200) and eluted stagewise, using chloroform and methanol. Specifically, chloroform, chloroform/methanol (100:1), chloroform/methanol (50:1) and chloroform/methanol (20:1) were successively eluted. The eluates were then analyzed by thin-layer chromatography [WAKOGEL B-5, developing solvent: chloroform/methanol (9:1), color reagent: iodine vapor, ninhydrin]. The eluted fractions exhibiting only the spot at $R_f = 0.35$ were collected and concentrated under reduced pressure to give 19.6 g of 2-methyl-3-aminomethyl-1-phenyl-4-isopropylpyrazolone (II) (yield 80%) as an oily product.

(b) 2-Methyl-3-bromomethyl-1-phenyl-4-isopropylpyrazolone (II) (30.9 g) was dissolved in 2000 ml of ethanol saturated with ammonia gas, and the solution was stirred at room temperature for 2 hours. After distilling the solvent off under reduced pressure, the reaction mixture was separated and purified by chromatographing on a column of silica gel by operating as in (a), above, to give 9.8 g (yield 40%) of 2-methyl-3-aminomethyl-1-phenyl-4-isopropylpyrazolone (II).

(c) Aspirin (14.4 g, 0.08 mole) was dissolved in 400 ml of chloroform, after which the solution was cooled to 0° C. Dicyclohexylcarbodiimide (18.2 g, 0.088 mole) was then added to the solution followed by stirring the mixture for 30 minutes and thereafter adding 19.6 g (0.08 mole) of 2-methyl-3-aminomethyl-1-phenyl-4-isopropylpyrazolone (II) obtained in either (a) or (b), above. The mixture was then stirred at room temperature for 24 hours. The precipitate of dicyclohexylurea formed was filtered off, and the solvent was distilled off under reduced pressure.

The residue was dissolved in 150 ml of chloroform, and this solution was added to a column packed with 1.8 liters of silica gel (WAKOGEL G-200), and its stagewise elution was performed as in (a), above, using chloroform and methanol. The eluates were analyzed by thin-layer chromatography [under the same conditions as in (a), except that iodine vapor and sulfuric acid were used as color reagent]. The eluted fractions exhibiting only the spot at $R_f=0.52$ were collected and concentrated under reduced pressure. The concentrate was purified by crystallizing from ethyl acetate to give 25.4 g (yield 80%) of N-3'a-propylphenazonyl-2-acetoxybenzamide (I).

This product is white crystals melting at 140°–141° C. This product dissolves readily in methanol, ethanol and acetone and dissolves fairly well in chloroform but is practically insoluble in water. In thin-layer chromatography (WAKOGEL B-5, color reagent: iodine vapor, sulfuric acid) this compound exhibits an $R_f=0.52$ when chloroform/methanol (9:1) is used as the developing solvent and an $R_f=0.23$ when ether is used as the developing solvent.

Elementary analysis:

|  | C | H | N |
|---|---|---|---|
| Calcd. (%) for $C_{23}H_{25}N_3O_4$: | 67.81 | 6.14 | 10.32 |
| Found (%): | 67.82 | 6.07 | 10.29 |

EXAMPLE 2

Pharmaceutical Compositions
Tablets:

The following ingredients are contained in the amounts indicated in each tablet (500 mg).

| AIA | 250.0 mg |
|---|---|
| Cornstarch (exipient)* | 120.0 mg |
| Lactose (excipient)* | 122.5 mg |
| Hydroxypropyl cellulose (binder)* | 5.0 mg |
| Talc (lubricant)* | 1.5 mg |
| Magnesium stearate (lubricant)* | 1.0 mg |
| Total | 500.0 mg |

*Japanese Pharmacopeia

Granules:

The following ingredients are contained in the amounts indicated in each gram of the granules.

| AIA | 500.0 mg |
|---|---|
| Lactose (exipient) | 250.0 mg |
| Cornstarch (exipient) | 200.0 mg |
| Crystalline cellulose (disintegrator) | 30.0 mg |
| Hydroxypropyl cellulose (binder) | 20.0 mg |
| Total | 1000.0 mg |

We claim:

1. Aspirin-isopropylantipyrine of the following formula

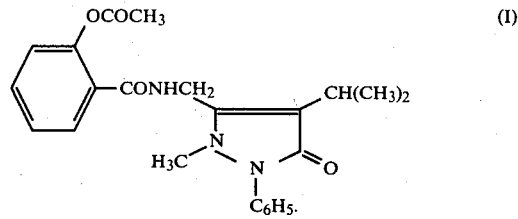

(I)

2. An analgetic, antipyretic or anti-inflammatory pharmaceutical composition composed of a pharmaceutically effective amount of aspirin-isopropylantipyrine of the following formula

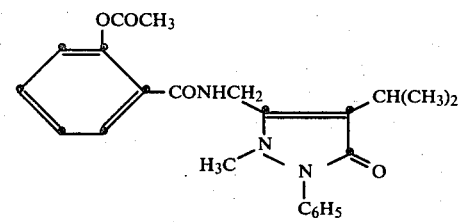

and a pharmaceutically acceptable carrier or diluent.

3. A pharmaceutical composition of claim 2 wherein the amount contained of the compound of the formula (I) is about 10% to 99% by weight based on the weight of the composition.

4. A method of treating patients requiring an analgetic, antipyretic or anti-inflammatory treatment, said method being characterized by administering aspirin-isopropylantipyrine of the following formula

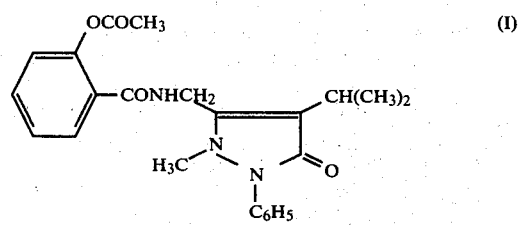

(I)

in a dosage of about 0.02 to about 0.08 g/kg-body per day.

* * * * *